United States Patent [19]

Strickland et al.

[11] Patent Number: 4,845,781

[45] Date of Patent: Jul. 11, 1989

[54] DISPOSABLE HAND COVERING FOR HANDLING CONTAMINATED MATERIAL

[75] Inventors: Donald G. Strickland, Roswell; Charles N. Bruner, Marietta, both of Ga.

[73] Assignee: Vadax, Inc., Atlanta, Ga.

[21] Appl. No.: 148,954

[22] Filed: Jan. 27, 1988

[51] Int. Cl.⁴ .................................... A41D 19/00
[52] U.S. Cl. .................................... 2/161 R; 2/167; 2/168; 294/1.3; 383/4
[58] Field of Search ............. 2/16, 158, 159, 167, 2/168; 15/227; 119/95; 294/1.3; 383/4

[56] References Cited

U.S. PATENT DOCUMENTS

| | | | |
|---|---|---|---|
| 2,106,348 | 1/1938 | Hall et al. | 2/168 |
| 2,641,767 | 6/1953 | La Rosa | 2/168 |
| 2,821,718 | 2/1958 | Hall et al. | 2/168 |
| 3,225,360 | 12/1965 | Keilen, Jr. et al. | 2/167 |
| 3,739,418 | 6/1973 | Yonaites et al. | 294/1.3 |
| 3,813,121 | 5/1974 | Marvin | 294/1.3 |
| 3,850,467 | 11/1974 | Johnson | 15/104.8 |
| 4,215,886 | 8/1986 | Naderi et al. | 294/1.3 |
| 4,667,697 | 7/1987 | Hayes | 383/4 |

FOREIGN PATENT DOCUMENTS

84/02640  7/1984  World Int. Prop. O. .

Primary Examiner—Werner H. Schroeder
Assistant Examiner—Jeanette F. Chapman
Attorney, Agent, or Firm—Foley & Lardner, Schwartz, Jeffery, Schwaab, Mack Blumenthal & Evans

[57] ABSTRACT

A disposable hand covering having a stiffened cuff is disclosed. The hand covering can be used to handle contaminated material and can then be removed by the wearer. The stiffened cuffs allow easy removal without contact with the contaminated outside of the hand covering. When the hand covering is removed, it everts to form a pouch. After eversion of the hand covering, sealing means on the stiffened cuffs allow closure of the pouch. The contaminated outside of the hand covering and any contaminated material which was held by the covered hand is contained within the pouch, allowing for safe disposal of the hand covering and its contents.

17 Claims, 3 Drawing Sheets

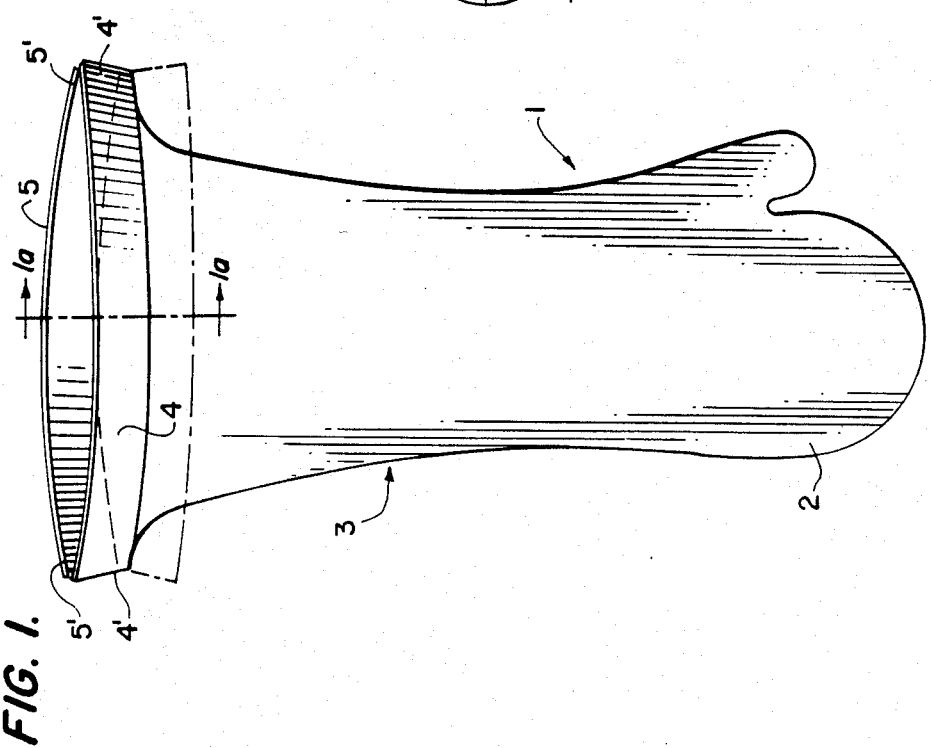
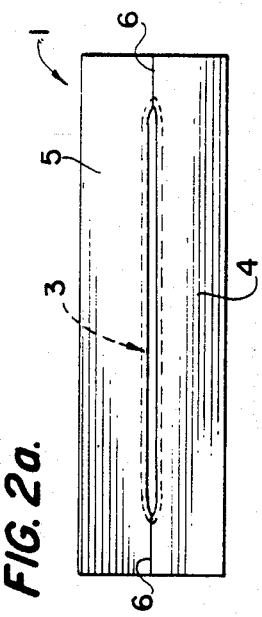
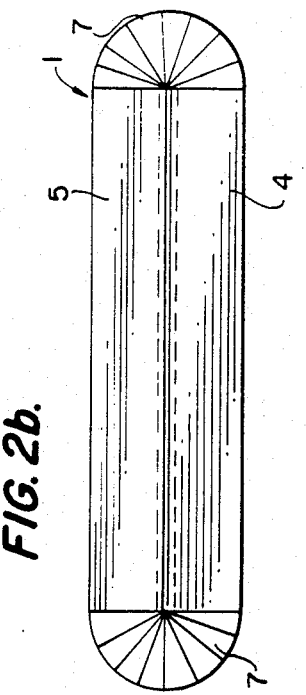
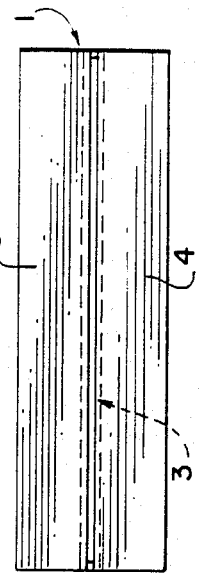
FIG. 1.
FIG. 2a.
FIG. 2b.
FIG. 2c.

DISPOSABLE HAND COVERING FOR HANDLING CONTAMINATED MATERIAL

BACKGROUND OF THE INVENTION

This invention relates to a disposable hand covering for handling contaminated material and more particularly to a disposable hand covering for containment of contaminated material in which the hand covering has a stiffened cuff to allow removal of the hand covering without contaminating the hands of the wearer.

Many types of disposable gloves have been developed. These disposable gloves are often used in cleanup operations. However, once these gloves are used, contaminant material clinging to the glove presents an additional unwanted source of contamination. This is true even if the contaminated glove is turned inside out. Often, disposal is to a temporary nonprotected container followed by removal to a sealed, leak-proof container. Prior to removal to the sealed container, there is the risk of secondary exposure to humans handling the discarded gloves.

U.S. Pat. No. 4,677,697 discloses a cleanup glove which is turned inside out after use and sealed to become a disposal bag, eliminating the need for special glove disposal means. However, although this glove contains the contaminated material, the wearer runs the risk of self-contamination in removing the glove. Removal of the glove is achieved in the normal way, by grasping both the inside and outside edges of the cuff and stripping the glove from the hand. In view of the high risk level associated with certain types of contaminated material, any contact with the outside of the glove by the wearer must be minimized.

SUMMARY OF THE INVENTION

It is therefore an object of the present invention to provide a disposable hand covering for the handling of contaminated material which can be removed by the wearer without contacting the outside of the glove.

It is a further object of the invention to provide a disposable hand covering for the handling of contaminated material which is turned inside out on removal to provide a leak-proof disposal bag for the contaminated material.

It is yet another object of the invention to provide a disposable hand covering which stays in position on the wearer's hand without relying on the friction of the glove with the wearer's hand.

It is another object of the invention to provide a disposable hand covering to collect, contain and confine contaminated material while minimizing risk to the wearer from the contaminated material.

In accomplishing the foregoing objects, there has been provided in accordance with the present invention a disposable hand covering comprising a hand portion, an arm portion attached to the hand portion, and a pair of stiffened cuffs attached to the end of the arm portion. The cuffs may have end portions which extend beyond the width of the arm portion. In this case the arm portion is flared as it approaches the cuffs.

The hand covering can be used to handle contaminated material and can then be removed by the wearer. The stiffened cuffs allow easy removal without contact with the contaminated outside of the hand covering. When the hand covering is removed, it everts to form a pouch. After eversion of the hand covering, sealing means on one or both of the stiffened cuffs allow closure of the pouch. The contaminated outside of the hand covering and any contaminated material which was held by the covered hand is contained within the pouch, allowing for safe disposal of the hand covering and its contents.

Other objects and features of the present invention will become apparent from the following detailed description considered in connection with the accompanying drawings, which disclose the features of the invention. It is to be understood, however, that the drawings and detailed description are designed for the purpose of illustration only, and are not limiting.

BRIEF DESCRIPTION OF THE DRAWINGS

FIG. 1 shows the hand covering in its fully extended state.

FIGS. 2a–2c show three embodiments of the stiffened cuffs.

DESCRIPTION OF THE PREFERRED EMBODIMENTS

Figure 4A:
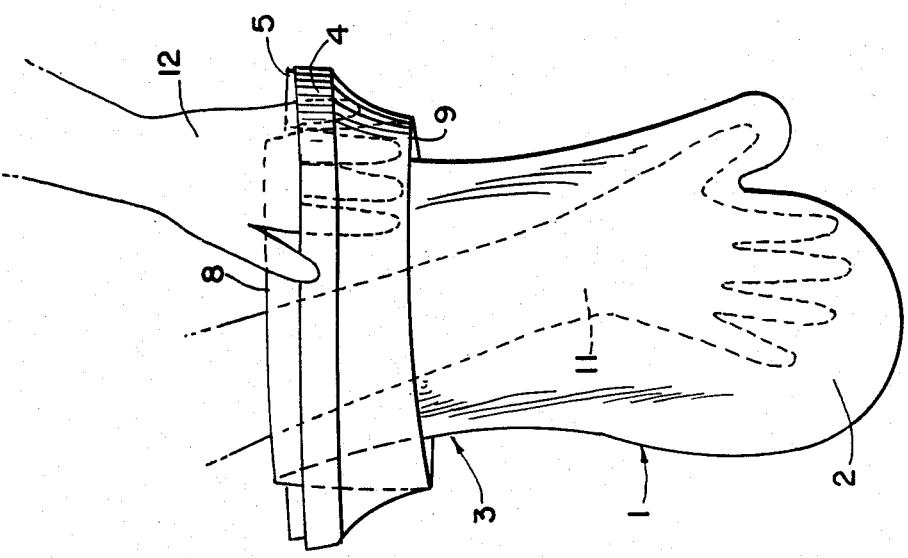
FIGS. 4a–4c show the removal of the hand covering by the wearer.

A disposable hand covering 1 according to the present invention is shown in FIG. 1. For convenience, hand portion 2 has been shown in the shape of a mitten. The hand covering may also take the form of a glove, or a simple pouch with no finger portions. The particular embodiment chosen will depend on the degree of manipulation required by the task to be performed by the wearer. For purposes of the following discussion, the inside of the glove will refer to that side of the glove which contacts the wearer's hand during use. The outside of the glove will refer to that side of the glove which contacts the contaminated material.

Hand covering 1 can be made of a variety of materials, in a manner well known in the art. By way of example, hand covering 1 can be made of any leakproof and flexible homopolymer, copolymer, or coextrusion that is capable of resisting punctures from fingernails or rings. Suitable materials include polyolefins, particularly polyethylene, polyvinyl chloride, latex, nylon, rubber or polyester and coextrusions thereof. Thicknesses in the range of about 0.5 to 10 mils are suitable. The thickness will depend on the strength and puncture resistance of the material chosen. For example, with polyvinyl chloride the preferred range would be about 6–8 mils, whereas with a conventional polyolefin (e.g., polyethylene or polyproplyene) the preferred range would be about 4–6 mils. Improved high-strength polymers, e.g., coextrusions of optionally copolymerized polyethylene, allow thicknesses of the order of 1–2 mils, or less, to be used.

Hand covering 1 can be made from separate sheets or a flattened tube of plastic. The plastic can be sealed and then cut along the outside of the seal, or the two steps can be reversed, i.e., the plastic can be first be cut to the desired shape and then sealed near the edges. In the latter case, excess material can be trimmed immediately after sealing, or at a later stage in the manufacturing process. The sealing can be by any of several well-known techniques, e.g., by heat, laser, ultrasonic bonding or the application of RF power. Alternatively, when the material is latex, hand covering 1 can be made by a dip method to produce a hand covering without seams, in the manner used to make surgical gloves.

Certain polyvinyl chlorides are also susceptible to a dip method.

Hand covering 1 is shown with long arm portion 3 which terminates in cuffs 4 and 5. Cuffs 4 and 5 are made of a material which is stiff relative to the material of hand portion 2 and arm portion 3. The stiffness of the cuff must be such that it is self-supporting, i.e. the cuff when grasped at an edge shows no tendency to fold back on itself under the force of gravity. Furthermore, when grasped at the two end portions 4',4' and bent into a curve, the material resists the bending, creating a tension by which the material attempts to return to its original flattened state.

During eversion of hand covering 1, cuffs 4, 5 must flip to the dotted line position shown in FIG. 1. The design of cuffs 4, 5 must allow for this flipping action. For example, if a surgical glove was modified so that the upper portion was stiff enough to resist bending, the glove would be virtually impossible to remove. Similarly, if cuffs 4, 5 were one circular cuff of stiffened material, or were rigidly attached along the outer edge of end portions 4', 5', this flipping action would be greatly constrained, making removal of hand covering 1 difficult or impossible.

Various embodiments of cuffs 4, 5 are shown spread apart in FIGS. 2a–2c. If desired, cuffs 4, 5 can be attached in any manner which does not interfere with the flipping action. For example, in a preferred embodiment, shown in FIG. 2a, the lower edges of cuffs 4, 5 (adjacent long arm portion 3) may be continuous at attachment regions 6. Attachment regions 6 can be scored, or otherwise weakened, to assist in the flipping action. The configuration of FIG. 2a assures proper alignment of cuffs 4, 5 for sealing after removal of hand covering 1.

In an alternative embodiment, the plastic material of arm portion 3 is used to loosely attach cuff ends 4' and 5'. In this case, it is advantageous to provide the plastic material in fluted or accordion configuration 7, as shown in FIG. 2b, to allow ample material between cuff ends 4', 5' so that the flipping of cuffs 4, 5 is not constrained.

Although the present description refers to two cuffs, it is apparent that the embodiments of FIGS. 2a–2b might also be described as one cuff having two portions. The important consideration is that the design be such that the flipping action is not constrained. In the embodiment of FIG. 2c, cuffs 4, 5 are not attached.

In order to maintain cuffs 4, 5 in their flipped-up state prior to donning of the glove, it may be advantageous to provide a weak sealant on the inside of end portions 4', 5' so that the insides of end portions 4', 5' are weakly attached to each other.

The stiffened cuffs according to the present invention provide control during donning and removal of hand covering 1. Furthermore, the wearer's arm bends the stiffened cuff into a curve, creating a tension which maintains the position of hand covering 1 on the wearer's hand without the necessity of a form fit. In those embodiments in which hand covering 1 is not form-fitting, the use of powder on the inside of hand covering 1 may be avoided. This eliminates the introduction of powder into open cuts on the wearer's hands and the undesirable feeling which remains after the removal of powdered gloves. (It should be noted that the necessity for using powder is also partially a function of the particular material used. With certain materials, the use of powder may still be desired even when a form fit is not used.)

The stiffened cuffs also allow the unique flipping action which prevents the necessity of grasping any outside portion of the glove during removal. After removal, the two stiffened cuffs are easily aligned for sealing.

In a preferred embodiment, cuffs 4, 5 are wider than long arm portion 3. Extra end portions 4', 5' allow better control during removal of hand covering 1. Long arm portion 3 is flared at the top to accommodate the increased width. The flare need not extend all the way to the end of the cuffs. When there is no flare arrangement at the top of long arm portion 3, there is a potential for leakage at the point where long arm portion 3 meets cuffs 4, 5. Thus, the wider cuffs and flare arrangement allow for both better control and decreased leakage.

Materials useful for construction of cuffs 4, 5 include plastic or board stock. Board stock is preferred because of lower manufacturing costs. Moreover, board stock can be easily printed with a legend indicating contaminated material is contained within hand covering 1 after eversion.

The thickness of the board-stock cuff can vary from about 20 to 60 mils, with about 30–35 mils being a preferred range. Because board stocks vary considerably, e.g., in density, the actual thickness required will vary depending on the board stock selected. Moreover, it has been found that the manner in which the cuff is made will affect the stiffness achieved with a given board stock. For example, the stiffness of a one-and-a-half-inch cuff made from a 32-mil board stock is less than that of a one-and-a-half-inch cuff made by folding a three-inch-wide 16-mil board stock in half to give a total thickness of 32 mils. In other words, the fold itself introduces additional stiffness. The fold provides the added advantage of a safer contoured edge.

In a preferred embodiment, the cuff of FIG. 2a is made from 6-inch-wide 16-mil board stock folded accordion-style into four one-and-a-half-inch segments (three folds). The middle fold is cut to provide the opening through which the wearer's hand passes, leaving uncut regions 6 on FIG. 2a. The other two folds result in one-and-a-half-inch, double-thickness (i.e., 32 mils) cuffs. The two thicknesses of each cuff are sealed together.

Cuffs 4, 5 can be attached to long arm portion 3 by an adhesive or heat seal. In a preferred embodiment, board stock is sealed with adhesive to long arm portion 3. It is not necessary for the material of long arm portion 3 to completely cover cuffs 4, 5, but there must be sufficient overlap of the arm portion and the cuffs to allow a secure attachment. If a compatible material is used, cuffs 4, 5 can be heat sealed to long arm portion 3.

One or both of cuffs 4, 5 are provided with sealing means on the outside of cuffs 4, 5 and end portions 4', 5'. In a preferred embodiment, a cohesive material is used. A cohesive material is a material which has a greater affinity for itself than it has for other materials. Thus, it has a minimum tack, but forms a strong bond when it comes in contact with itself. A perfect cohesive material for the present invention would have a high affinity for itself and for the cuff material, and a low affinity for all other materials, i.e. clothing, skin, etc.

Alternatively, an adhesive material may be used. The adhesive material may be a hot melt adhesive, which may be applied in a patterned fashion. The adhesive may also take the form of double-sided tape. It may be necessary with such a material to provide a cover strip, such as silicone release paper, which is removed prior to sealing. The cover strip prevents the adhesive from sticking to other materials. The sealing means may also comprise any of the microencapsulated adhesives which are well-known in the art.

Because hand covering 1 contains contaminated material, the sealing means should be such that it cannot be readily reopened after sealing. In a preferred embodiment, the strength of the sealing means is greater than that of the hand covering material, so that it is necessary to destroy the hand covering to obtain access to the contents.

Figure 3:
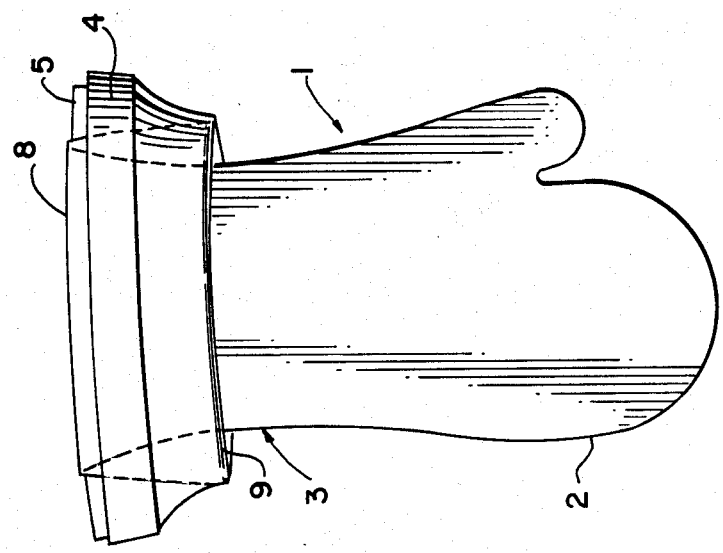
FIG. 3 shows the hand covering in its folded state.

Long arm portion 3 allows a special folding arrangement which facilitates removal of the hand covering without contact by the wearer with the contaminated outside of the hand covering. The special folding arrangement is shown in FIG. 3. Long arm portion 3 is first folded down over the outside of hand covering 1 to form fold 8. This is the singlefold arrangement used for donning surgical gloves without contaminating the sterile outside of the glove, commonly referred to as "the technique cuff." In the present invention, long arm portion 3 is then folded back on itself at fold 9 to form a double cuff arrangement. The upper edges of cuffs 4, 5 should closely approach fold 8 in order to minimize any possibility of contamination of the inside portion of the glove. This "double technique cuff" not only prevents contact with the outside of the hand covering during donning, but also prevents contact with the outside of the hand covering during removal. A weak sealant may be used to maintain alignment of the double technique cuff until the hand covering is removed.

The hand covering is donned by grasping at fold 8 and pulling hand portion 2 onto wearer's hand 11. Typically, cuffs 4, 5 will surround the wearer's forearm, although a longer version of hand covering 1 would also be possible.

Figure 4B:
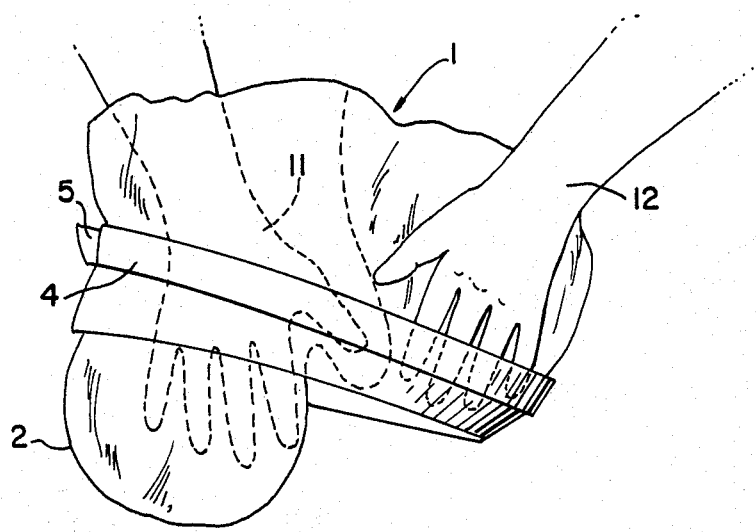
Figure 4C:
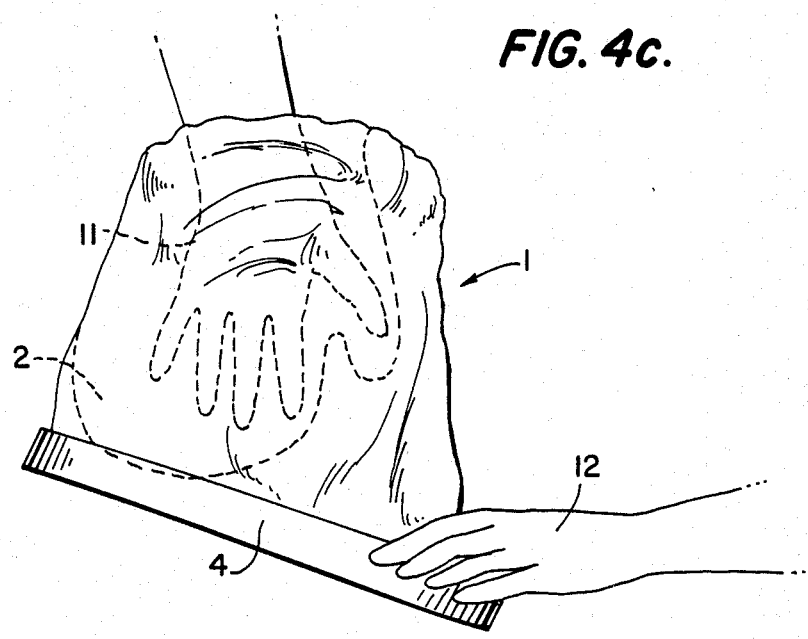

FIGS. 4a-4c show removal of hand covering 1. Free hand 12 is inserted in the pocket created by the folded-back portion of long arm portion 3. Hand 12 contacts only the inside of hand covering 1. Movement of hand 12 downward (i.e., toward hand portion 2) brings the fingers of hand 12 in contact with the inside of fold 9. Further movement downward begins eversion of hand covering 1. When the end of hand portion 2 is reached, a natural flipping action of cuffs 4, 5 occurs as a result of the stiffness of the cuffs. Hand 12 can complete this flipping action to bring the two cuffs into alignment for sealing. Hand 11 is removed from hand covering 1 and any contaminated material held by hand 11 is now sealed in everted hand covering 1. Thus, hand covering 1 is used to collect, contain and confine.

Hand covering 1 can also be used in its fully extended state. This is especially advantageous for house cleaning chores. As in the previous embodiment, the wearer's arm bends the stiffened cuff into a curve, creating a tension which maintains the position of hand covering 1 on the wearer's hand without the necessity of a form fit. Typically the cuffs will surround the upper arm of the wearer, although shorter versions are also possible. Of course, if the same glove is used in both embodiments, the cuffs will surround a lower portion of the wearer's arm when used in the folded embodiment than they will when used in the extended embodiment. Because of the stiffened cuffs, it is still possible to remove the gloves without contacting the outside of the glove. The wearer simply inserts the free hand between the cuff and the arm. The tension of the cuffs on the wearer's arm causes resistance and a natural pocket will form as a result of the downward motion of the free hand. Cuffs 4, 5 slide down the wearer's arm and when the end of hand portion 2 is reached the stiffened cuffs flip to form an everted pouch as in the folded embodiment. However, the "double technique cuff" is preferred to provide greater assurance against the possibility of accidental contact with the outside of the hand covering.

Although the invention has been described in some detail by way of illustration, it will be apparent that changes and modifications may be practiced without departing from the spirit and scope of the invention.

What is claimed is:

1. A disposable hand covering comprising:
   a hand portion;
   an arm portion attached to said hand portion; and
   a stiffened cuff having two portions attached to the end of said arm portion.

2. A disposable hand covering according to claim 1, wherein said cuffs have end portions which extend beyond the width of said arm portion.

3. A disposable hand covering according to claim 2, wherein said arm portion is flared onto the end portions of said cuffs.

4. A disposable hand covering according to claim 2, wherein said stiffened cuffs have a weak sealant on the inside of said end portions such that the insides of said end portions are weakly attached to each other.

5. A disposable hand covering according to claim 1, wherein said stiffened cuffs comprise a material selected from the group consisting of board stock and plastic.

6. A disposable hand covering according to claim 5, wherein the thickness of said cardboard stock cuff is from about 20 to 60 mils.

7. A disposable hand covering according to claim 5, where the thickness of said cardboard stock cuff is from about 30-35 mils.

8. A disposable hand covering according to claim 5, wherein said arm and hand portions comprise a flexible and leakproof homopolymer, copolymer or coextrusion of two or more homopolymers or copolymers.

9. A disposable hand covering according to claim 5, wherein said arm and hand portions comprise material selected from the group consisting of latex, polyolefins, polyvinyl chloride, nylon, polyesters, and rubber.

10. A disposable hand covering according to claim 5, wherein said material comprises polyethylene coextruded with at least one other polymer layer.

11. A disposable hand covering according to claim 8, wherein the thickness of the material used in said arm and hand portions is from about 0.5 to 10 mils.

12. A disposable hand covering according to claim 10, wherein the thickness of the material used in said arm and hand portions is from about 1 to 2 mils.

13. A disposable hand covering according to claim 1, further comprising sealing means on the outside of said stiffened cuffs.

14. A disposable hand covering according to claim 13, wherein said sealing means is selected from the group consisting of cohesive and adhesive materials.

15. A disposable hand covering according to claim 14, further comprising a cover strip for said sealing means.

16. A disposable hand covering according to claim 1, wherein said arm portion further comprises a double technique cuff to facilitate donning and removal of said hand covering without contact with its outer surface.

17. A method of handling contaminated material, comprising the steps of:

donning of the hand covering claimed in claim 16 by a wearer;

handling of the contaminated material by the wearer's gloved hand;

insertion of the wearer's free hand into the double technique cuff of the hand covering;

eversion of the hand covering; and sealing of the cuffs.

* * * * *